(12) United States Patent
Garth et al.

(10) Patent No.: US 7,141,031 B2
(45) Date of Patent: Nov. 28, 2006

(54) CERVICAL COLLAR WITH END-SUPPORTED CHIN STRAP

(75) Inventors: Geoffrey Garth, Long Beach, CA (US); Charles Patterson, Long Beach, CA (US)

(73) Assignee: W. G. Holdings, LLC., Long Beach, CA (US)

( * ) Notice: Subject to any disclaimer, the term of this patent is extended or adjusted under 35 U.S.C. 154(b) by 189 days.

(21) Appl. No.: 10/444,201

(22) Filed: May 23, 2003

(65) Prior Publication Data

US 2004/0176713 A1 Sep. 9, 2004

Related U.S. Application Data

(60) Provisional application No. 60/382,937, filed on May 24, 2002.

(51) Int. Cl.
*A61F 5/00* (2006.01)
(52) U.S. Cl. .................. 602/18; 128/DIG. 23
(58) Field of Classification Search ............. 602/5, 602/18–19, 17; 128/DIG. 23
See application file for complete search history.

(56) References Cited

U.S. PATENT DOCUMENTS

| | | | | |
|---|---|---|---|---|
| 4,643,174 A | * | 2/1987 | Horiuchi | 602/318 |
| 4,712,540 A | * | 12/1987 | Tucker et al. | 602/18 |
| 5,097,824 A | * | 3/1992 | Garth | 602/18 |
| 5,230,698 A | * | 7/1993 | Garth | 602/18 |
| 5,797,863 A | * | 8/1998 | Køhnke | 602/18 |
| 6,090,058 A | * | 7/2000 | Traut et al. | 602/18 |
| 6,494,854 B1 | * | 12/2002 | Visness et al. | 602/18 |

* cited by examiner

*Primary Examiner*—Michael A. Brown
(74) *Attorney, Agent, or Firm*—Rutan&Tucker, LLP

(57) ABSTRACT

The cervical collar has three principal pieces: a back panel, a main collar body, and a chin piece. The chin piece is permanently attached to the main collar body and is only attached at its ends to the main collar body so that the center portion of the chin piece can adjust to chin configuration. The back panel engages behind the neck and is tightened with respect to the main collar body to properly support the patient's head and protect the cervical spine. The chin piece adjusts to the patient's chin configuration because it is sufficiently flexible and only supported away from the chin area. Each of the pieces has a foam cushioning layer.

20 Claims, 5 Drawing Sheets

CERVICAL COLLAR WITH END-SUPPORTED CHIN STRAP

CROSS-REFERENCE

This application relies on U.S. patent application Ser. No. 60/382,937, filed May 24, 2002 for priority.

FIELD OF THE INVENTION

This invention is directed to a cervical collar for supporting the cervical vertebrae, particularly when a person is injured and cervical damage is suspected.

BACKGROUND OF THE INVENTION

When a human body is stressed, such as by injury, various kinds of damage may occur. Stress to the cervical vertebrae may cause nerve damage and, when that high on the spinal cord, nerve damage can lead to significantly debilitating paralysis. The extent of paralysis is related to which particular cervical vertebra is adjacent to the damaged nerve. Therefore, it is essential to provide a cervical collar which properly supports the head and neck of an accident victim until the scope and nature of the damage is determined.

SUMMARY OF THE INVENTION

In order to aid in the understanding of this invention, it can be stated in essentially summary form that it is directed to a cervical collar with end-supported chin piece. The cervical collar is formed of a back piece positioned behind the neck and a main collar body engaged on the upper chest of the patient just below his neck. Each is padded, and they are attached together around the neck. A chin piece is secured to the main collar body at each side thereon. The chin piece is of flexible sheet material and engages under the chin of the patient. It is supported only adjacent its ends so that the center portion under the patient's chin is unsupported allowing it to conform itself to the shape of the patient's chin.

It is, thus, a purpose and advantage of this invention to provide a cervical collar with end-supported chin piece so that the chin piece engages under the chin of the patient and can conform by its flexibility to the shape of the patient's chin.

It is a further purpose and advantage of this invention to provide a cervical collar with end-supported chin piece wherein the chin piece is made of flexible sheet material and is secured to the rest of the collar structure only adjacent its ends so that the center portion thereof may flex to accommodate patients with different chin configuration.

Other purposes and advantages of this invention will become apparent from a study of the following portion of the specification, the claims and the attached drawings.

DESCRIPTION OF THE PREFERRED EMBODIMENTS

Figure 1:
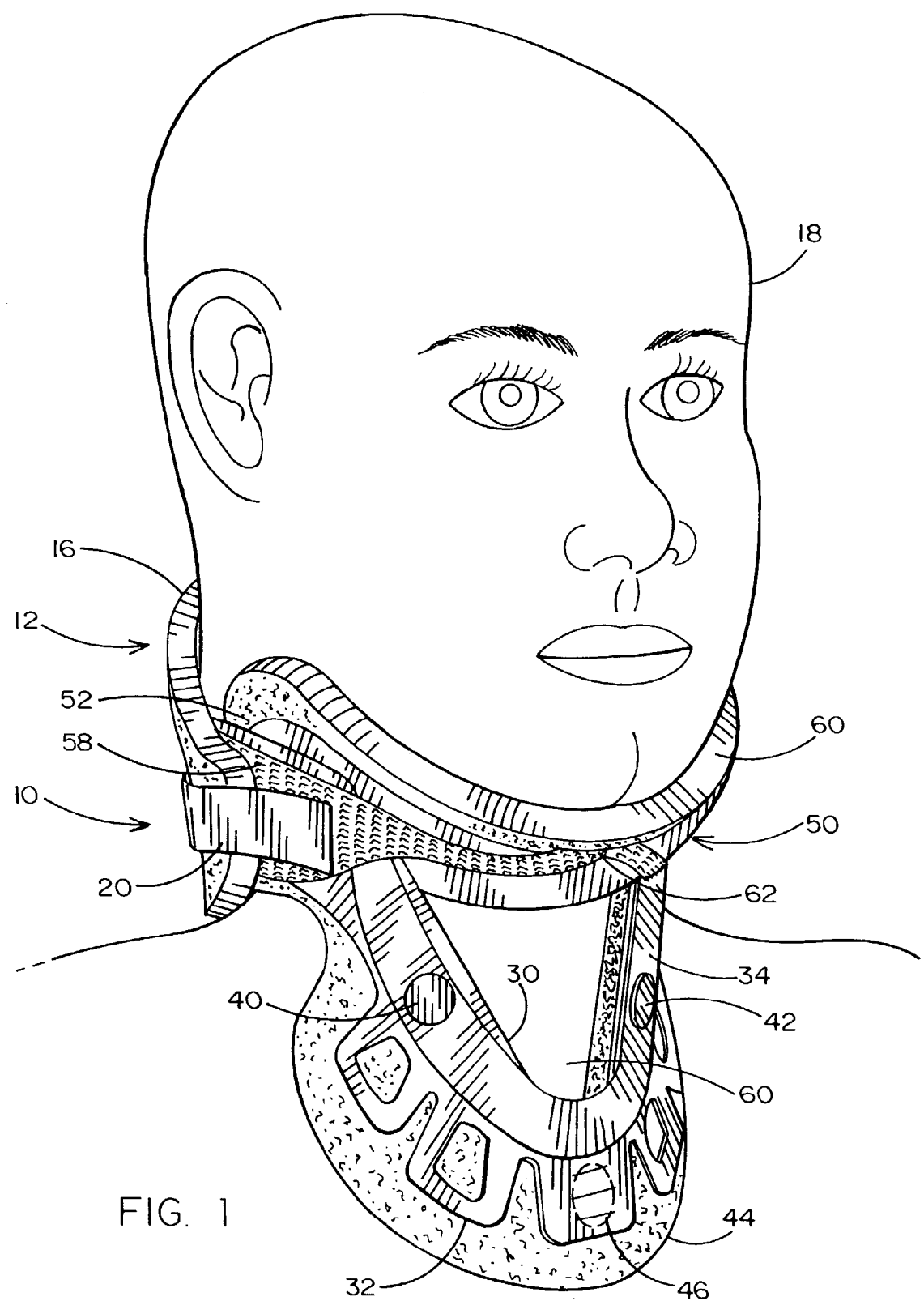
FIG. 1 is a perspective view of the cervical collar with end-supported chin piece of this invention shown on a patient for his cervical spine support.
Figure 2:
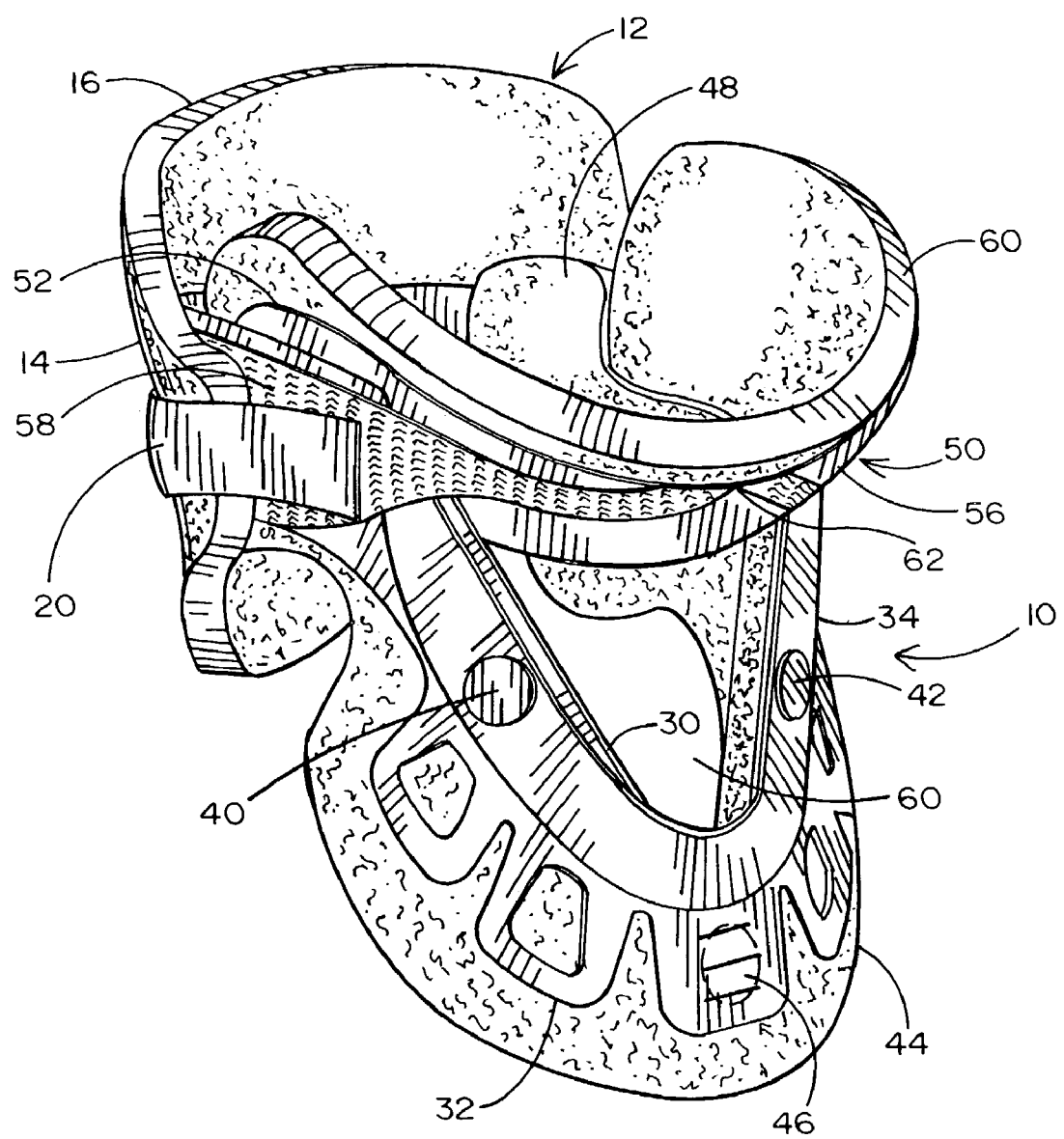
FIG. 2 is a similar view, without the patient.
Figure 3:
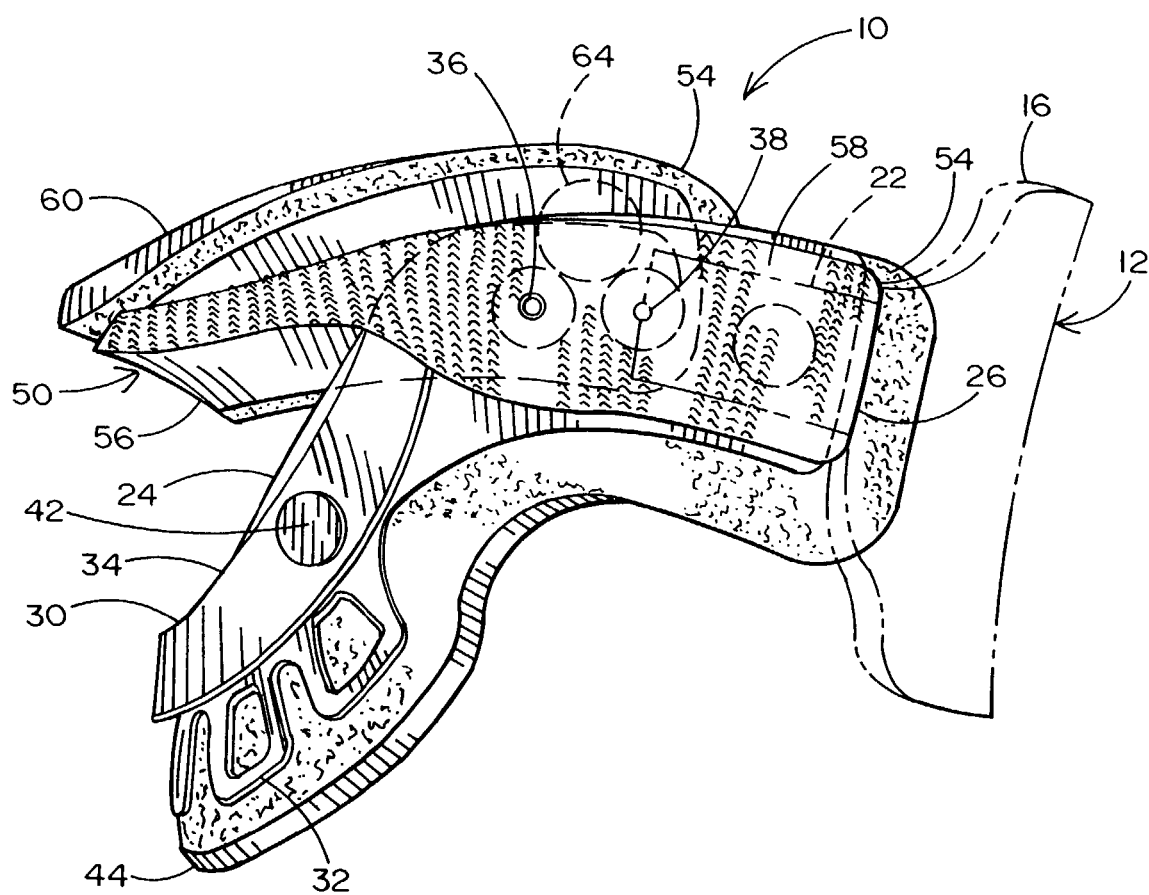
FIG. 3 is a left side elevational view thereof with the cervical collar in the assembled configuration.

The first preferred embodiment of the cervical collar with end-supported chin piece is generally indicated at 10 in FIGS. 1, 2, 3 and 4. The cervical collar 10 is comprised of three principal structural parts. The back panel 12 is seen in FIGS. 1, 2 and 3. The back panel 12 comprises a sheet 14 of flexible polymer composition material which carries a padding layer 16 thereon. The padding layer 16 is preferably a foam polymer layer. The back panel 12 is configured to extend around the back of the neck of the patient 18. Extending forward from the back panel on each side is a flexible attachment band for securing the back panel to the main collar body 24. The attachment band 20 is seen in FIGS. 1 and 2. A similar band 22 is attached to the left side of the back panel and is seen in dashed lines in FIG. 3. These bands are preferably half of a hook and loop fastener system.

Figure 4:
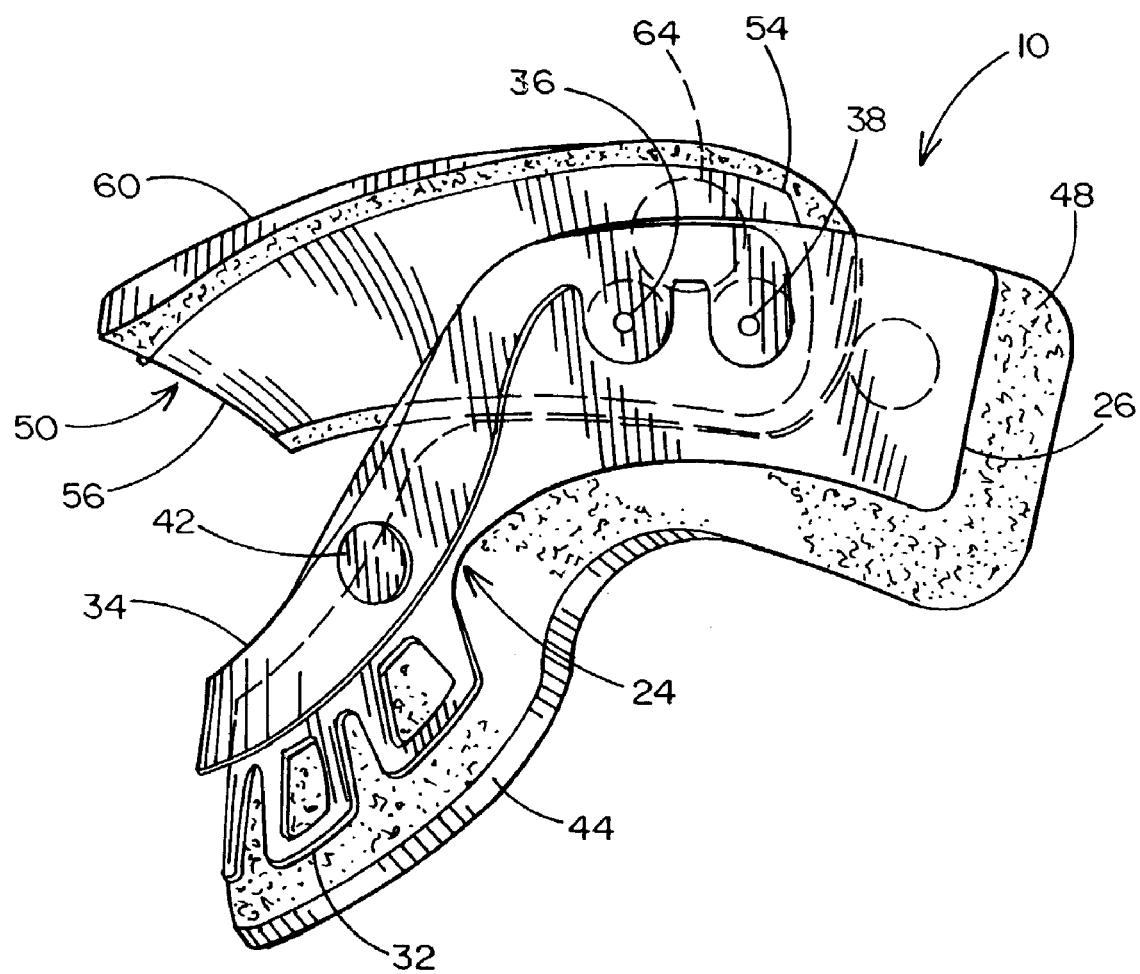
FIG. 4 is an view similar to FIG. 3, but with the upper velcro layer removed.

Main collar body 24 is formed of a sheet of flexible synthetic polymer composition material. It engages from the sides of the neck of the patient down over his chest. The back edge 26 on the left side is seen in FIGS. 3 and 4. The back edge on the right side is obscured in FIGS. 1 and 2, because it is inside the near edge of the back panel. The back edges of the main collar body about lie in the plane of the cervical spine. From the back edge, the main collar body extends forward and sweeps down to form an upper edge 30, which is sufficiently far down on the chest to define a tracheotomy access opening at the front of the patient's neck. The lower edge of the main collar body has tabs 32 thereon. The tabs have notches between and openings therein to provide a progressively smaller cross section from the free lower edge of the solid portion of the main collar body. The tabs provide an easier transition between the constraining effect of the collar 10 and the unsupported surface adjacent thereto. As seen in FIGS. 1–4, the sides of the main collar body sweep forward off the sides of the neck and then downward to engage over the patient's clavicle to obtain firm support of the cervical collar from the patients skeletal structure.

In order to strengthen the main collar body 24, strengthener 34 is a generally U-shaped structure of sheet synthetic polymer composition material cut into U-shape. At its upper end, it is attached to the main collar body 24 by means of rivets 36 and 38, see FIGS. 3 and 4. At its U-shaped lower portion, which generally follows the U-shaped center portion of the main collar body 24, is attached by rivets 40 and 42, see FIGS. 1 and 2. Rivet 42 is also seen in FIGS. 3 and 4. The back end of the strengthener band 34 is also attached to the main collar body 24 at rivets 36 and 38. Similar attachment is provided at the opposite side.

Padding layer 44 underlies the main collar body 24 and is preferably a layer of synthetic foam material having fabric attached to each side. The inside fabric layer is suitable for engagement against the patient, while the outside fabric layer on the foam padding layer is suitable to be engaged by the hook portion of a hook-and-loop fastener. The padding layer 16 is similar. Padding layer 44 is attached to the inside of the main collar body 24 by the hook portion of a hook-and-loop fastener. A disc 46 of hook fastener is attached to the inside of the lower front of the main collar body 24, see FIG. 1. Other such discs are preferably fastened on the underside of the main collar body 24, for example, near the rivets 40 and 42. The padding layer extends up and back along the interior of the main collar body 24 and terminates in an ear, which extends back beyond the back ends of the main collar body. One of the ears is indicated at 48 in FIG. 2. The other side is similar.

The third principal structural part of the cervical collar 20 is the chin piece, generally indicated at 50 in FIGS. 1, 2, 3 and 4. The chin piece 50 is formed of flexible sheet synthetic polymer material and is configured so that, when the ends 52 and 54 are substantially vertical where they lie inside the ends of the main collar body, the forward chin-supporting section 56 lies forward at an angle between 30 and 45 degrees to the horizontal, as seen in FIGS. 3 and 4. The chin piece is attached to the main collar body by two rivets at each side. The two rivets on the left side are indicated at 36 and 38 in FIGS. 3 and 4. There are similar rivets on the right side. These rivets are hidden under the hook fastener band 58, which is seen in FIGS. 1, 2 and 3. The view of FIG. 4 is shown with this hook fastener band removed to show the positioning of the rivets. As seen in FIGS. 3 and 4, the rivets are close to the back end of both the main collar body and the chin piece.

The entire center section of the chin piece in the forward direction beyond the forward rivet 36 and its companion rivet on the other side is unsupported. The forward rivet is no further forward than halfway from the patient's mandibular joint to the center of his chin. Support for the chin at the center of the chin piece is provided by the stiffness of the chin piece. The chin piece is sufficiently stiff to provide adequate support, but it is flexible enough to be able to bend substantially to the patient's chin contours. The entire width of the front of the chin piece over the entire tracheotomy opening 60 is not engaged or supported by any other structure. The only structural support for the chin piece is at its rivets near its back ends, as previously stated.

Padding layer 60 covers the inside of the chin piece 50. It is a polymer foam padding layer with a suitable fabric on the inside surface for skin contact. The outside of the padding layer is covered with a fabric which can be engaged by the hook portion of a hook-and-loop fastener system. Band 58 of the hook portion of the hook-and-loop fastener is wrapped round the back end 26 for a short way. The ear 48 engages thereon and is releasibly retained by the portion of the band 58. The band 58 extends forward and is folded over the top edge of the chin piece at its front center. This folded-over portion is indicated at 62 in FIGS. 1 and 2. At that location, it lies on the inside of the chin piece at its top edge. It is at this location that the padding layer is attached at its front center to the hook fastener band. The padding layer is secured to the inside of chin piece 60 adjacent its back end by attachment disc 64, as shown in FIGS. 3 and 4.

When it is required for the support of his head and neck, the cervical collar 10 is placed on the patient 18. The main collar body and chin piece are a permanently attached structure, and the respective padding layers are in position. The main collar body 24 is placed against the chest with the chin piece 50 under the chin of the patient. The back panel 12 is placed behind the neck of the patient and overlaps the outside of the main collar body on both sides, as seen in FIGS. 1 and 2. The main collar body and chin piece are thrust back at the same time the back panel is thrust forward. Attachment bands 20 and 22 on the back panel are pulled forward and attached to the band 58 on both sides. The application of the collar 10 on the patient should be sufficiently firm so that the tabs on the main collar body and the tabs on the back panel are resiliently bent. This applies resilient stabilization to the cervical spine and head of the patient.

Figure 5:
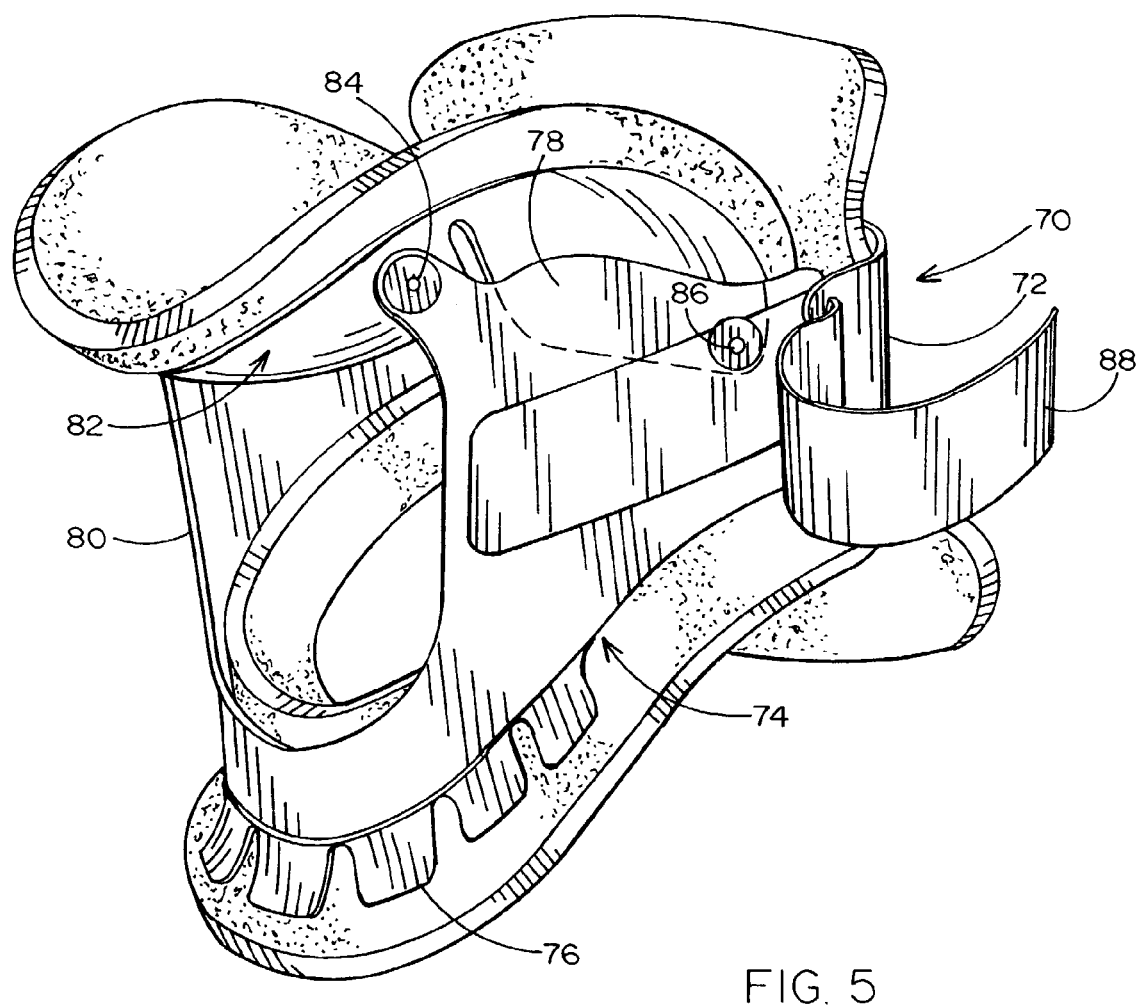
FIG. 5 is a front left perspective view of a second preferred embodiment of the cervical collar with end-supported chin piece of this invention, similar to the view of FIG. 2.

Another preferred embodiment of the cervical collar with end-supported chin piece is seen in FIG. 5 and is generally indicated at 70. The cervical collar 70 is comprised of three principal parts. It has a back panel 72, which is the same as back panel 12 except that it is taller. Main collar body 74 extends forward and downward and rests upon the chest of the patient. It has tabs 76 to provide a transition which is more gradual than a hard edge. The tabs may have configuration which changes their resiliency as a function of the distance from the principal part of the main collar body. As compared to the main collar body of the cervical collar 10, the main collar body 74 has an arm 78 which extends upward, with one arm on each side of the tracheotomy opening 80. Both the back panel and main collar body have a suitably configured padding layer thereunder. The padding layer is of polymer foam material with its inside suitable for body contact and its outside suitable for attachment by hook-type fasteners. The inside of the back panel and inside of the main collar body are each provided with portions of hook-type fasteners so that the padding material is removably attached thereto.

Chin piece 82 is permanently attached to the main collar body by means of two rivets on each side. Rivets 84 and 86 are shown on the near side of FIG. 5. The forward rivet 84 is no closer to the center of the chin strap than half the distance from the patient's mandibular joint to the center of the chin strap. There are similar rivets on the far side. This structure is very similar to the structure of cervical collar 10, except that the rivet mountings are farther apart. The chin piece also has a padding layer of the nature described above. The flexibility of the chin piece between the front two rivets, of which rivet 84 is one, and the distance between the front rivets is sufficient so that the chin piece can adjust to the configuration of the patient's chin. The chin piece is unsupported between its rivets and relies upon its own stiffness to provide support, together with the necessary flexibility to achieve the proper chin support configuration. Hook-and-loop fastener strap 88 is attached to the main collar body, extends through a slot in the back panel and extends forward to attach onto itself. A similar fastener strap is provided on the opposite side so that the collar 70 can be tightened to the appropriate firmness to properly support the patient's head and stabilize his cervical spine.

This invention has been described in its presently preferred embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A cervical collar comprising:
    a main collar body configured to overlie the upper chest of at patient and extend over his shoulders substantially to the spinal plane;
    a flexible chin supporting piece, having no midline support and being secured to the main collar body only adjacent to its ends; and
    a back panel coupled to the main collar body, and configured to engage the hack of the neck of the patient.

2. The cervical collar of claim 1 wherein at least one of said chin supporting piece, main collar body and said back panel have padding attached thereto.

3. The cervical collar of claim 2 wherein said padding comprises a foam polymer.

4. The cervical collar of claim 1 wherein at least one of said main collar body and said back panel has flex tabs along the edge thereof.

5. The cervical collar of claim 4 wherein at least some of said tabs have a base and a tip, with the base being wider than the tip.

6. The cervical collar of claim 1, further comprising a hook-and-loop fastener that couples said main collar body and said back panel.

7. The cervical collar of claim 6 having right and left lateral portions, each of which operates as a continuous extension of the main collar body.

8. The cervical collar of claim 7 wherein the right and left lateral portions are riveted to the main collar.

9. The cervical collar of claim 1 wherein the chin piece has left and right rivets lateral to the midline.

10. A cervical collar comprising:
a main collar body having a padded chest portion and a portion that extends over a patient's shoulder;
a chin piece having two lateral arms coupled to the main collar body, and a mid-section that is supported entirely by the lateral arms;
an adjustment mechanism thtu adjusts the chin piece relative to the main collar body; and
a back panel removably coupled to the main collar body.

11. The cervical collar of claim 10 wherein said back panel carries a padding.

12. The cervical collar of claim 10 wherein said back panel has flexible tabs.

13. The cervical collar of claim 12 wherein said flexible tabs are of increasing cross section from their tips to the brace where they are integral with said main collar body.

14. The cervical collar of claim 10 wherein there is an opening in said main collar body to provide access for tracheotomy, and there is a strengthening layer adjacent said opening to provide adequate strength around said opening for said main collar body.

15. The cervical collar of claim 11 wherein said padding layer is attached to said cervical collar by hook fasteners.

16. The cervical collar of claim 10 wherein said back panel is attached to said main collar body by means of hook-and-loop fasteners.

17. The cervical collar of claim 16 wherein a portion of said book-and-loop fasteners for attachment of said back panel also serves as attachment structure for attaching said main collar body padding thereto said main collar body.

18. The cervical collar of claim 10 wherein said chin piece is attached to said back panel through the main body.

19. The cervical collar of claim 18 wherein said chin piece is attached to said back panel through the main body by at least one river.

20. The cervical collar of claim 19 wherein the chin piece has right and left rivet attachments.

* * * * *